United States Patent [19]

Kriloff

[11] Patent Number: Plant 5,729

[45] Date of Patent: Apr. 29, 1986

[54] ROSE PLANT KRIBALOR

[75] Inventor: Michel Kriloff, Antibes, France

[73] Assignee: Jackson & Perkins Company, Medford, Oreg.

[21] Appl. No.: 652,837

[22] Filed: Sep. 21, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Klarquist, Sparkman, Campbell, Leigh & Whinston

[57] ABSTRACT

A hybrid tea rose variety having an upright plant, orange colored blooms on upper sides of petals and near white on the reverse, little fragrance, large prickles, and good resistance to rose powdery mildew.

1 Drawing Figure

This present invention relates to a new and distinct variety of rose plant of the hybrid tea class which was originated by me by crossing an unnamed variety with an unnamed variety.

The primary objective of this breeding was to produce a new rose variety of the hybrid tea class producing blooms of a novel orange and white color. This objective was substantially achieved along with other desirable improvements as evidenced by the following unique combination of characteristics which are outstanding in the new variety and which distinguish it from its parents, as well as from all other varieties of which I am aware:

1. Upright plant of bush form.
2. Blooms of orange color on upper sides of petals with a near white reverse.
3. Little or no fragrance.
4. Large prickles hooked downward.
5. Good resistance to rose powdery mildew.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:

*Seed parent.*—Unnamed variety.

*Pollen parent.*—Unnamed variety.

Classification:

*Botanical.*—Rosa hybrid.

*Commercial.*—Hybrid tea.

FLOWER

Observations made from specimens grown at Irvine, Calif. in November.

Blooming habit: Continuous.

Bud:

*Size.*—1" when petals start to unfurl.

*Form.*—Blunt top, ovoid.

*Color.*—When sepals first divide, near white, except for pigmentation where exposed between sepals of Red 53A and slight coloration from pigment on upper layers of petals. When half blown, upper side of petals Orange-Red 32; lower side of petals near white.

*Sepals.*—Color: Green 138A. Three appendaged sepals lightly appendaged. Two unappendaged sepals hairy edged.

*Receptacle.*—Color: Green 138A. Shape: Funnel. Size: Broad, small. Surface: Smooth.

*Peduncle.*—Length: Short. Surface: Slightly glandular. Color: Light green. Strength: Stiff, erect.

*Opening.*—Petals fold outward with little curling.

Bloom:

*Size.*—Large. Average open size: 4" to 5".

*Borne.*—Singly.

*Stems.*—Long, strong.

*Form.*—When first open, flat. Permanence: Retains its form to the end; outer petal edges slightly curled.

*Petalage.*—Number of petals under normal conditions: 27-30.

*Color.*—Center of flower: Upper side of petals Orange-Red 32; reverse side of petals near white; base of petals have large white area which blends to yellow at point of attachment. Major color: Orange-Red 32 with white reverse.

*Variegations.*—Occasional vegetative streaks on outer petals.

*Discoloration.*—General tonality at end of first days: Slight deepening of color. Third day: Color deepens where exposed to Red 42B.

*Fragrance.*—None.

Petals:

*Texture.*—Thick.

*Shape.*—Nearly round; nearly as wide as long.

*Form.*—Tips slightly recurved.

*Arrangement.*—Imbricated. Petaloids in center: few.

*Persistence.*—Drop off cleanly.

*Lastingness.*—On the plant, long. As cut flower, long.

Reproductive parts:

*Anthers.*—Medium, many. Color: Yellow. Arrangement: Regular around styles.

*Filaments.*—Color: Light yellow.

*Pollen.*—Gold yellow.
*Styles.*—Color: White at base.
*Stigmas.*—Color: White.

PLANT

Form: Bush.
Growth: Vigorous, upright.
Foliage: Number of leaflets on normal mid-stem leaves: 5.
*Size.*—Large.
*Quantity.*—Normal.
*Color.*—New foliage: Near Greyed Purple 187B, quickly developing into green. Old foliage: Green 136B.
Leaflets:
*Shape.*—Elliptic.
*Texture.*—leathery on upper side.
*Edge.*—Serrated.
*Serration.*—Single, small.
*Petiole.*—Rachis: Color: Green. Underside: Prickles.

*Disease resistance.*—Resistant to mildew under normal growing conditions at Irvine, Calif.
Wood:
*New wood.*—Color: Reddish. Bark: Smooth.
*Old wood.*—Color: Green. Bark: Smooth.
Prickles:
*Quantity.*—On main canes from base: Ordinary. On laterals from main canes: Ordinary.
*Form.*—Long, hooked downward.
*Color when young.*—Green and red.
*Position.*—Irregular.
Small prickles:
*Quantity.*—On main stalks: None. On laterals: None.

I claim:

1. A new and distinct variety of rose plant of the hybrid tea class, substantially as herein shown and described, characterized particularly as to novelty by the unique combination of its upright plant habit, resistance to rose powdery mildew, downward hooked thorns, bi-color orange and white blooms.

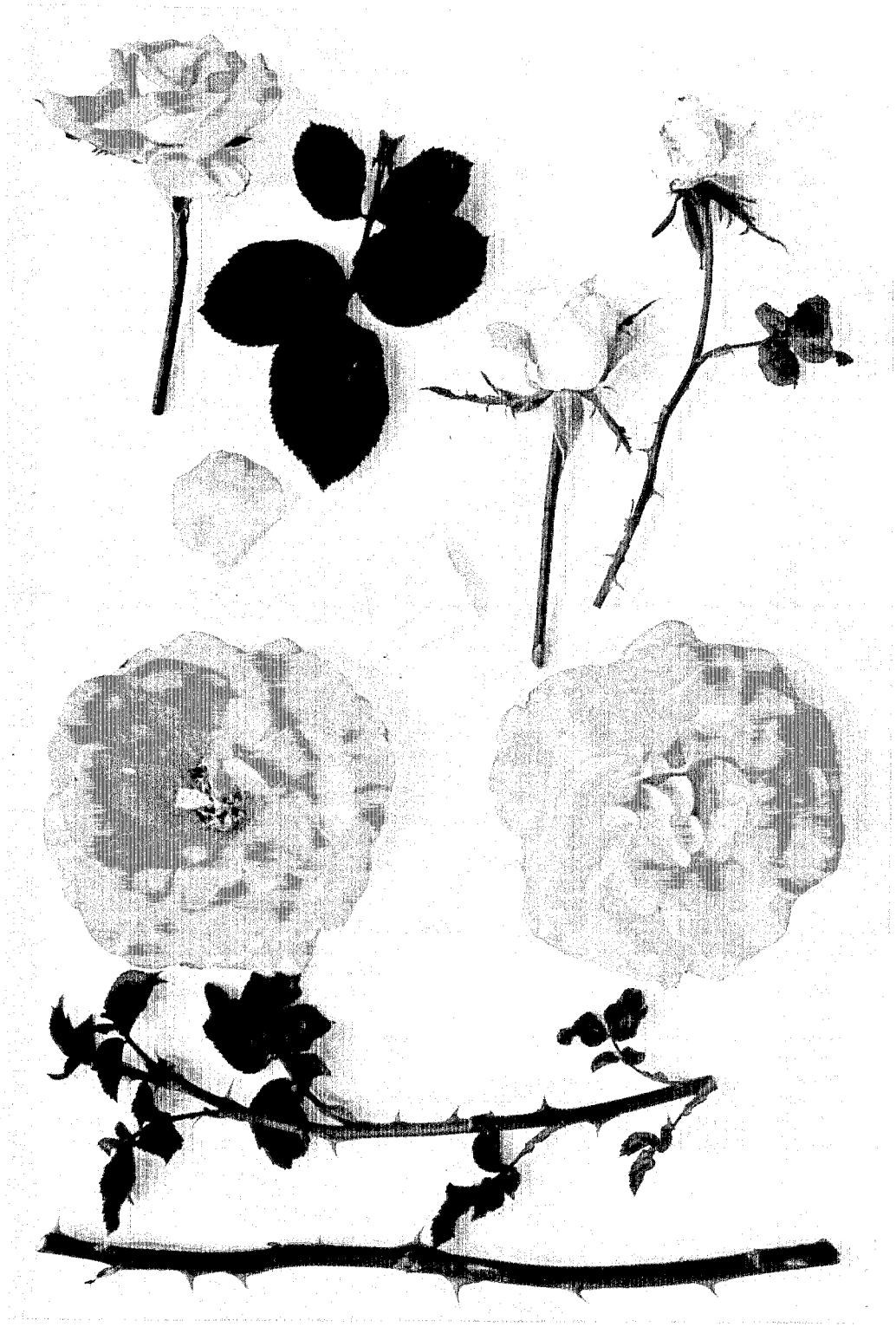

* * * * *